United States Patent
Pollack et al.

(10) Patent No.: US 10,139,422 B2
(45) Date of Patent: Nov. 27, 2018

(54) THROUGHPUT OPTIMIZING REAGENT DISTRIBUTION

(71) Applicant: Siemens Healthcare Diagnostics Inc., Tarrytown, NY (US)

(72) Inventors: Benjamin S. Pollack, Budd Lake, NJ (US); Colin Mellars, Dover, NJ (US); Baris Yagci, Whippany, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 40 days.

(21) Appl. No.: 14/759,172

(22) PCT Filed: Jan. 9, 2014

(86) PCT No.: PCT/US2014/010909
§ 371 (c)(1),
(2) Date: Jul. 2, 2015

(87) PCT Pub. No.: WO2014/110282
PCT Pub. Date: Jul. 17, 2014

(65) Prior Publication Data
US 2015/0338427 A1    Nov. 26, 2015

Related U.S. Application Data

(60) Provisional application No. 61/750,549, filed on Jan. 9, 2013.

(51) Int. Cl.
*G01N 35/00* (2006.01)
*C40B 30/02* (2006.01)

(52) U.S. Cl.
CPC ......... *G01N 35/0092* (2013.01); *C40B 30/02* (2013.01); *G01N 35/0095* (2013.01); *G01N 2035/0094* (2013.01); *G01N 2035/00326* (2013.01); *Y10T 436/115831* (2015.01)

(58) Field of Classification Search
CPC ........... G01N 35/0092; G01N 35/0095; G01N 2035/0094; G01N 2035/00326
See application file for complete search history.

(56) References Cited

U.S. PATENT DOCUMENTS

| | | | |
|---|---|---|---|
| 5,358,691 A * | 10/1994 | Clark | B01L 3/08 422/63 |
| 6,319,469 B1 | 11/2001 | Mian et al. | |
| 7,998,432 B2 | 8/2011 | Rousseau | |
| 8,043,562 B2 | 10/2011 | Tomasso et al. | |
| 2005/0220671 A1 | 10/2005 | Stein et al. | |
| 2008/0020469 A1 * | 1/2008 | Barnes | G01N 35/0092 436/46 |
| 2008/0113440 A1 | 5/2008 | Gurney et al. | |
| 2011/0020179 A1 | 1/2011 | Yue et al. | |
| 2011/0201121 A1 | 8/2011 | Kaartinen | |
| 2012/0115138 A1 | 5/2012 | Deigner et al. | |
| 2012/0275885 A1 * | 11/2012 | Furrer | G01N 35/00732 414/222.02 |

FOREIGN PATENT DOCUMENTS

| | | |
|---|---|---|
| EP | 1 248 170 A1 | 10/2002 |
| WO | 2005/009202 A2 | 2/2005 |
| WO | 2012/059839 A2 | 5/2012 |

OTHER PUBLICATIONS

PCT International Search Report and Written Opinion dated Apr. 29, 2014 (15 pages).
Extended EP Search Report dated Aug. 4, 2016 of corresponding European Application No. 14738228.7, 4 Pages.

* cited by examiner

*Primary Examiner* — Paul S Hyun

(57) ABSTRACT

Methods and systems for performing tests in an in vitro diagnostic environment provide for a substantially optimized distribution of testing reagents amongst a plurality of analyzers. The system and method can include steps of identifying a plurality of expected tests to be performed by a plurality of analyzer modules, determining information about the capabilities of the plurality of analyzer modules, and receiving, at the processor, data reflecting which of the plurality of tests are incompatible. Further steps can include calculating a substantially optimal distribution of the plurality of expected tests amongst the plurality of analyzer modules, allocating reagents to each of the plurality of analyzer modules by facilitating distribution of a plurality of reagents to selected analyzer modules in response to the step of calculating, and automatically scheduling a plurality of samples to undergo tests at the plurality of analyzer modules.

19 Claims, 7 Drawing Sheets

| Cycle | P1 | P2 | Incubate | Luminosity |
|---|---|---|---|---|
| 1 | A1 | | | |
| 2 | A2 | A1 | | |
| 3 | A3 | A2 | A1 | |
| 4 | | A3 | A2 | A1 |
| 5 | | | A3 | A2 |
| 6 | | | | A3 |

Test A: P1→P2→Inc.→Lumo     Table 10

| Cycle | P1 | P2 | Incubate | Luminosity |
|---|---|---|---|---|
| 1 | | B1 | | |
| 2 | B1 | B2 | | |
| 3 | B2 | B3 | B1 | |
| 4 | B3 | | B2 | B1 |
| 5 | | | B3 | B2 |
| 6 | | | | B3 |

Test B: P2→P1→Inc.→Lumo     Table 12

| Cycle | P1 | P2 | Incubate | Luminosity |
|---|---|---|---|---|
| 1 | A1 | | | |
| 2 | ■ | A1 | | |
| 3 | | B1 | A1 | ■ |
| 4 | B1 | | ■ | A1 |
| 5 | | | B1 | B1 |
| 6 | | | | |

Table 14

Fig. 1

| Test Name | RAT Incompatible | Chemical Incompatible |
|---|---|---|
| TA | TB | TC |
| TB | TA | |
| TC | | TA |

Panel 1: TA, TB, TC          Table 16

| Test Name | RAT Incompatible | Chemical Incompatible |
|---|---|---|
| TD | | TF |
| TE | | |
| TF | TD | TE |

Panel 2: TD, TE, TF          Table 18

Fig. 2

| Panel | Analyzer 1 | Analyzer 2 |
|---|---|---|
| P1 | TA, TB, TC | |
| P2 | | TD, TE, TF |

Table 20

| Panel | Analyzer 1 | Analyzer 2 |
|---|---|---|
| P1 | TB, TC | TA |
| P2 | TF | TD, TE |

Table 22

Fig. 3

Table 24

THROUGHPUT OPTIMIZING REAGENT DISTRIBUTION

CROSS-REFERENCE TO RELATED APPLICATIONS

This application claims priority to U.S. provisional application Ser. No. 61/750,549 filed Jan. 9, 2013, which is incorporated herein by reference in its entirety.

TECHNOLOGY FIELD

The present invention relates in general to managing reagents or tests within one or more analyzers in a laboratory environment and, more particularly to systems and methods for allocation of testing resources within one or more analyzers. Embodiments of the present invention are particularly well suited, but in no way limited, to computerized methods for optimizing allocation of reagents or tests within an automation system.

BACKGROUND

In vitro diagnostics (IVD) allows labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers (analyzers) onto which fluid containers, such as tubes or vials containing patient samples have been loaded. The analyzer extracts a liquid sample from the vial and combines the sample with various reagents in special reaction cuvettes or tubes (referred to generally as reaction vessels). In some conventional systems, a modular approach is used for analyzers. A lab automation system can shuttle samples between one sample processing module (module) and another module. Modules may include one or more stations, including sample handling stations and testing stations (e.g., a unit that can specialize in certain types of assays or can otherwise provide testing services to the larger analyzer), which may include immunoassay (IA) and clinical chemistry (CC) stations. Some traditional IVD automation track systems comprise systems that are designed to transport samples from one fully independent module to another standalone module. In a typical workflow in a diagnostic laboratory, multiple diagnostic tests are ordered for individual samples. For example, a doctor may order a plurality of immunoassays on a patient sample to search for different antibodies. While the doctor's goal in ordering the tests is to make a diagnosis based on a desired set of facts, the tests may not be an optimal combination for utilizing an analyzer efficiently. For example, tests may be incompatible when run in succession. Tests may be incompatible in two ways. First, tests may use reagents that react poorly with reagents of another test. The chemical incompatibility of these two tests may require additional wash cycles for any pipettes that may be shared between the tests. For example, a single reagent pipette may be used amongst a plurality of reagents. If multiple tests utilize that same reagent pipette tip and that reagent pipette is required to dispense chemically incompatible reagents in succession, the reagent pipette may have to waste a cycle doing an additional wash step to avoid contaminating the next test or the next reagent reservoir.

Another way that tests may be incompatible is that two tests may utilize incompatible resource allocation profiles. To operate with maximum efficiency, tests should begin each operation cycle of an analyzer module during steady-state operation of the analyzer. Where there is no competition for resources (such as pipettes, incubators, or detection instruments, such as luminescence detectors), it may be possible to schedule tests to begin each cycle. However, if tests utilize resources in different sequences or require exclusive use of resources for different periods of time, starting two tests in succession may create a competition between those two tests for the same resources during a later cycle.

In some instances, the chemistry of each test is calibrated with the assumption that each test will be completed within a certain amount of time after starting a test. For example, a test may be calibrated using a two-minute window between the addition of reagents and the observation of the reaction. A delay of three minutes between the reagent addition and the detection of results may affect the accuracy of the test. Accordingly, the start of tests may need to be delayed until all steps in the task can be scheduled without uncertain delays. This can result in skipped machine cycles where no tests begin. This can reduce the overall throughput of an analyzer and can increase the turnaround time of a batch of samples.

SUMMARY

Embodiments of the present invention address and overcome one or more of the above shortcomings and drawbacks by providing devices and systems for optimizing the allocation of reagents and test amongst a plurality of analyzers. This technology is particularly well-suited for, but by no means limited to, clinical laboratory systems that utilize analyzers to perform in vitro diagnostics with overlapping testing capability, with or without an automation system for shuttling patient samples between the analyzers.

According to one embodiment of the invention, a method for distributing sample tests in an IVD environment can include identifying a plurality of expected tests to be performed by a plurality of analyzer modules and determining information about the capabilities of the plurality of analyzer modules. A processor can receive data reflecting which of the plurality of tests are incompatible and calculate a substantially optimal distribution of the plurality of expected tests amongst the plurality of analyzer modules. The method can continue by allocating reagents to each of the plurality of analyzer modules by facilitating distribution of a plurality of reagents to selected analyzer modules in response to the step of calculating and scheduling a plurality of samples to undergo tests at the plurality of analyzer modules. At least a portion of the samples can be scheduled to traverse an automation system to undergo tests at more than one of the plurality of analyzer modules to complete a plurality of test panels.

According to one aspect of some embodiments, the step of identifying a plurality of expected tests can include receiving a list of scheduled tests for the plurality of samples from a laboratory information system. The step of identifying a plurality of expected tests can also include analyzing statistics from past tests to determine an approximation of the likelihood of expected tests to be used by upcoming sample batches. The step of identifying a plurality of expected tests can further include receiving, by the processor, input from an operator using a computerized interface.

According to another aspect of some embodiments, the step of determining information about the capabilities of the plurality of analyzer modules can include receiving, from a laboratory information system, a list of the plurality of analyzer modules and capability information sufficient to determine which analyzer modules are capable of performing each of the plurality of expected tests. The step of determining information about the capabilities of the plurality of analyzer modules can also include receiving, from a processor associated with at least a subset of the plurality of analyzers, capability information sufficient to determine whether that analyzer module is capable of performing each of the plurality of expected tests.

According to another aspect of some embodiments, the step of receiving data reflecting which of the plurality of tests are incompatible can include receiving an identification of which tests are chemically incompatible. The step of receiving data reflecting which of the plurality of tests are incompatible can also include receiving an identification of which tests are incompatible because they require allocation of resources in a conflicting manner.

According to yet another aspect of some embodiments, the step of calculating a substantially optimal distribution of the plurality of expected tests can include using a search algorithm to identify at least one solution that exceeds a compatibility threshold. The step of allocating reagents can include displaying a request to an operator to manually load reagents into each of the plurality of analyzer modules. The step of allocating reagents can also include communicating with a robotic device to automatically load reagents into each of the plurality of analyzer modules.

According to still another aspect of some embodiments, the step of scheduling the plurality of samples to undergo tests can include dispatching each of the plurality of samples to at least one analyzer module to have at least one test performed by the analyzer module. The step of scheduling the plurality of samples to undergo tests can also include scheduling each STAT sample within the plurality of samples to have all tests in a test panel performed by a single analyzer module.

According to another embodiment of the invention, a system for performing tests in an IVD environment can include a plurality of analyzer modules, each configurable to perform a respective plurality of tests, an automation system configured to transport samples between the plurality of analyzer modules, and at least one processor. At least a subset of the analyzer modules can be configurable to perform the same tests. The processor can be configured to perform steps of identifying a plurality of expected tests to be performed by the plurality of analyzer modules, determining information about the capabilities of the plurality of analyzer modules, and receiving data reflecting which of the plurality of tests are incompatible. The processor can then perform steps of calculating a substantially optimal distribution of the plurality of expected tests amongst the plurality of analyzer modules, allocating reagents to each of the plurality of analyzer modules by facilitating distribution of a plurality of reagents to selected analyzer modules in response to the step of calculating, and scheduling a plurality of samples to undergo tests at the plurality of analyzer modules, wherein at least a portion of the samples are scheduled to traverse an automation system to undergo tests at more than one of the plurality of analyzer modules to complete a plurality of test panels.

According to another embodiment of the invention, a non-transient machine-readable media contains instructions that configure a processor in an IVD environment to perform steps of identifying a plurality of expected tests to be performed by a plurality of analyzer modules, determining information about the capabilities of the plurality of analyzer modules, and receiving, at the processor, data reflecting which of the plurality of tests are incompatible. The instructions further include steps of calculating, using the processor, a substantially optimal distribution of the plurality of expected tests amongst the plurality of analyzer modules, allocating reagents to each of the plurality of analyzer modules by facilitating distribution of a plurality of reagents to selected analyzer modules in response to the step of calculating, and automatically scheduling a plurality of samples to undergo tests at the plurality of analyzer modules.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIG. 1 is a tabular view of various exemplary resource allocation tables that may be used with some embodiments;

FIG. 2 is a tabular view of various exemplary incompatibilities within test panels that may be used with some embodiments;

FIG. 3 is a tabular view of various allocation approaches for allocating tests within test panels that may be used with some embodiments;

DETAILED DESCRIPTION OF ILLUSTRATIVE EMBODIMENTS

Figure 4:
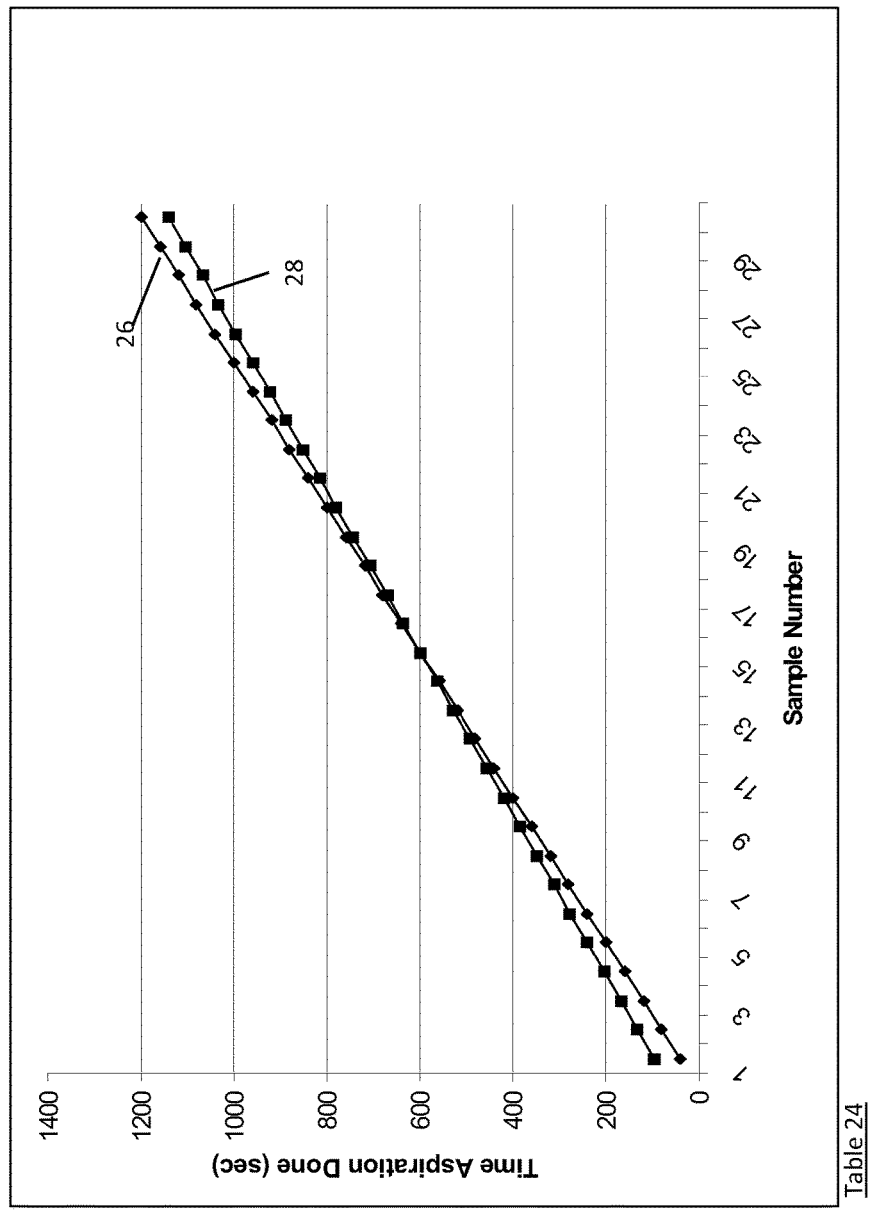
FIG. 4 is a graph depicting the performance of various allocations of tests in an exemplary system of analyzers that may be used with some embodiments.

Terms and Concepts Associated with Some Embodiments

Analyzer: Automated clinical analyzers ("analyzers") include clinical chemistry analyzers, automated immunoassay analyzers, or any other type of in vitro diagnostics (IVD) testing analyzers. Generally, an analyzer performs a series of automated IVD tests on a plurality of patient samples. Patient samples may be loaded into an analyzer (manually or via an automation system), which can then perform one or more immunoassays, chemistry tests, or other observable tests on each sample. The term analyzer may refer to, but is not limited to, an analyzer that is configured as a modular analytical system. A modular analytical system includes an integrated and extendable system comprising any combinations of a plurality of modules (which can include the same type of module or different types of modules) interconnected in a linear or other geometric configuration by an automation surface, such as an automation track. In some embodiments, the automation track may be configured as an integral conveyance system on which independent carriers are used to move patient samples and other types of material between the modules. Generally, at least one module in a modular analytical system is an analyzer module. Modules may be specialized or made redundant to allow higher throughput of analytical tasks on patient samples.

Analyzer module: An analyzer module is a module within a modular analyzer that is configured to perform IVD tests, such as immunoassays, chemistry tests, or other observable tests on patient samples. Typically, an analyzer module extracts a liquid sample from a sample vessel and combines the sample with reagents in reaction cuvettes or tubes (referred to generally as reaction vessels). Tests available in an analyzer module may include, but are not limited to, a subset of electrolyte, renal or liver function, metabolic, cardiac, mineral, blood disorder, drug, immunoassay, or other tests. In some systems, analyzer modules may be specialized or made redundant to allow higher throughput. The functions of an analyzer module may also be performed by standalone analyzers that do not utilize a modular approach.

Carrier: A carrier is a transportation unit that can be used to move sample vessels (and, by extension, fluid samples) or other items in an automation system. In some embodiments, carriers may be simple, like traditional automation pucks (e.g., passive devices comprising a holder for engaging a tube or item, a friction surface to allow an external conveyor belt in the automation track to provide motive force, and a plurality of sides that allow the puck to be guided by walls or rails in the automation track to allow the track to route a puck to its destination). In some embodiments, carriers may include active components, such as processors, motion systems, guidance systems, sensors, and the like. In some embodiments, carriers can include onboard intelligence that allows carriers to be self-guided between points in an automation system. In some embodiments, carriers can include onboard components that provide motive forces while, in others, motive forces may be provided by an automation surface, such as a track. In some embodiments, carriers move along automation tracks that restrict motion to a single direction (e.g., fore and aft) between decision points. Carriers may be specialized to a given payload in an IVD environment, such as having a tube holder to engage and carry a sample tube, or may include mounting surfaces suitable to carry different items around an automation system. Carriers can be configured to include one or more slots (e.g., a carrier may hold one or a plurality of sample vessels).

Central controller or processor: A central controller/processor (which may sometimes be referred to as a central scheduler) is a processor that is part of the automation system, separate from any processors onboard carriers. A central controller can facilitate traffic direction, scheduling, and task management for carriers. In some embodiments, a central controller can communicate with subsystems in the automation system and wirelessly communicate with carriers. This may also include sending trajectory or navigational information or instructions to carriers and determining which carriers should go where and when. In some embodiments, local processors may be responsible for managing carriers on local track sections, such as managing local queues. These local processors may act as local equivalents to central controllers.

Decision point: Decision points are points on an automation track where different navigational or trajectory decisions may be made for different carriers. A common example includes a fork in a track. One carrier may proceed without turning, while another may slow down and turn. Decision points may include stopping points at instruments, where some carriers may stop, while others may proceed. In some embodiments, deceleration zones ahead of turns may act as decision points, allowing carriers that will be turning to slow down to limit lateral forces, while others may proceed if not turning or if the motion profile for that carrier does not require slowing down. The decisions made at decision points can be made by processors onboard carriers, processors local to the track section, a central processor, or any combination thereof, depending on the embodiment.

Independent carrier: In some embodiments, carriers may be characterized as independently controlled carriers. Independently controlled carriers, are carriers with independently controlled trajectories. In some embodiments, independent carriers may be operating at the same time, on the same track, with carriers carrying one or a plurality of combinations of payloads that differ by size, weight, form factor, and/or content. The trajectories of each independently controlled carrier may be limited by a motion profile that includes maximum jerk, acceleration, direction, and/or speed for the carrier while moving in the automation system. The motion profile can limit or define the trajectory for each carrier independently. In some embodiments, a motion profile can be different for different sections of the automation system (e.g., in straight track sections vs. around curves to account for the added lateral forces while turning), for different carrier states (e.g., an empty carrier may have a different motion profile from a carrier transporting a sample or from a carrier transporting a reagent or other item), and/or for different carriers. In some embodiments, carriers can include onboard propulsion components that allow individual carriers to independently operate responsive to a motion profile or trajectory or destination instructions intended for each separate carrier.

Intelligent carrier/semi-autonomous carriers: In some embodiments, carriers may be characterized as intelligent carriers. An intelligent carrier is a carrier with onboard circuits that participates in motion, routing, or trajectory decisions. An intelligent carrier can include digital processors that execute software instructions to proceed along an automation surface responsive to the instructions or onboard analog circuits that respond to motion input (e.g., line follower circuits). Instructions may include instructions characterizing motion profiles, traffic, or trajectory rules. Some intelligent carriers may also include onboard sensors to assist onboard processors to route the carrier or make decisions responsive to the carrier's environment. Some intelligent carriers may include onboard components, such as motors or magnets, which allow the carrier to move responsive to control of an onboard processor.

In vitro diagnostics (IVD): In vitro diagnostics (IVD) are tests that can detect diseases, conditions, infections, metabolic markers, or quantify various constituents of bodily materials/fluids. These tests are performed in laboratory, hospital, physician office, or other health professional settings, outside the body of a patient. IVD testing generally utilizes medical devices intended to perform diagnoses from assays in a test tube or other sample vessel or, more generally, in a controlled environment outside a living organism. IVD includes testing and diagnosis of disease or quantifying various constituents of bodily materials/fluids based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with analyzers into which tubes or vials containing patient samples have been loaded. IVD can refer to any subset of the IVD functionality described herein.

Landmarks: In embodiments where carriers include onboard sensors, optical or other marks in track surfaces or locations viewable/sensible from track surfaces can act as landmarks. Landmarks can convey geographic information to carriers, such as a current location, upcoming stopping location, decision point, turn, acceleration/deceleration points, and the like.

Lab automation system: Lab automation systems include any systems that can automatically (e.g., at the request of an operator or software) shuttle sample vessels or other items within a laboratory environment. With respect to analyzers, an automation system may automatically move vessels or other items to, from, amongst, or between stations in an analyzer. These stations may include, but are not limited to, modular testing stations (e.g., a unit that can specialize in certain types of assays or can otherwise provide testing services to the larger analyzer), sample handling stations, storage stations, or work cells.

Module: A module performs specific task(s) or function(s) within a modular analytical system. Examples of modules may include: a pre-analytic module, which prepares a sample for analytic testing, (e.g., a decapper module, which removes a cap on top of a sample test tube); an analyzer module, which extracts a portion of a sample and performs tests or assays; a post-analytic module, which prepares a sample for storage after analytic testing (e.g., a recapper module, which reseals a sample test tube); or a sample handling module. The function of a sample handling module may include managing sample containers/vessels for the purposes of inventory management, sorting, moving them onto or off of an automation track (which may include an integral conveyance system, moving sample containers/vessels onto or off of a separate laboratory automation track, and moving sample containers/vessels into or out of trays, racks, carriers, pucks, and/or storage locations.

Payload: While exemplary carriers are described with respect to carrying patient samples, in some embodiments, carriers can be used to transport any other reasonable payload across an automation system. This may include fluids, fluid containers, reagents, waste, disposable items, parts, or any other suitable payloads.

Processor: A processor may refer to one or more processors and/or related software and processing circuits. This may include single or multicore processors, single or multiple processors, embedded systems, or distributed processing architectures, as appropriate, for implementing the recited processing function in each embodiment.

Pullouts, sidecars, offshoot paths: These terms may be used to refer to track sections that are off the main portion of a track system. Pullouts or sidecars may include chords, parallel tracks, or other suitable means for separating some carriers from a primary traffic pattern. Pullouts or sidecars may be configured to facilitate physical queues or allow certain carriers to stop or slow down without disrupting traffic on a main track section.

Samples: Samples refers to fluid or other samples taken from a patient (human or animal) and may include blood, urine, hematocrit, amniotic fluid, or any other fluid suitable for performing assays or tests upon. Samples may sometimes refer to calibration fluids or other fluids used to assist an analyzer in processing other patient samples.

STAT (short turnaround time) sample: Samples may have different priority assigned by a laboratory information system (LIS) or operator to assign STAT priority to samples that should take precedent over non-STAT samples in the analyzer. When used judiciously, this may allow certain samples to move through the testing process faster than other samples, allowing physicians or other practitioners to receive testing results quickly.

Station: A station includes a portion of a module that performs a specific task within a module. For example, the pipetting station associated with an analyzer module may be used to pipette sample fluid out of sample containers/vessels being carried by carriers on an integrated conveyance system or a laboratory automation system. Each module can include one or more stations that add functionality to a module.

Station/module: A station includes a portion of an analyzer that performs a specific task within an analyzer. For example, a capper/decapper station may remove and replace caps from sample vessels; a testing station can extract a portion of a sample and perform tests or assays; a sample handling station can manage sample vessels, moving them onto or off of an automation track, and moving sample vessels into or out of storage locations or trays. Stations may be modular, allowing stations to be added to a larger analyzer. Each module can include one or more stations that add functionality to an analyzer, which may be comprised of one or more modules. In some embodiments, modules may include portions of, or be separate from, an automation system that may link a plurality of modules and/or stations. Stations may include one or more instruments for performing a specific task (e.g., a pipette is an instrument that may be used at an immunoassay station to interact with samples on an automation track). Except where noted otherwise, the concepts of module and station may be referred to interchangeably.

Tubes/sample vessels/fluid containers: Samples may be carried in vessels, such as test tubes or other suitable vessels, to allow carriers to transport samples without contaminating the carrier surfaces.

Exemplary Embodiments

The above problems in the prior art have motivated the discovery of improved apparatus and methods for distributing tests and testing resources amongst a plurality of analyzers or modules. Specifically, by allowing multiple analyzers/modules to perform tests from the same test panel on samples-under-test, throughput can be increased within each analyzer and the overall analyzer system because conflicts (referred to as "incompatibilities") between tests on the same analyzer can be reduced or eliminated, reducing or eliminating wasted operational cycles within each analyzer or module.

In some embodiments of the present invention, throughput and turnaround times of batches of samples under test can be improved by selectively distributing tests between a plurality of analyzers that share an automation system. Tests for each sample have typically been performed entirely on a single analyzer. In some embodiments, a single test panel may be broken up across multiple analyzers to avoid incompatibilities between tests that may limit operating efficiency. Tests can be distributed to different analyzers to minimize incompatibilities. Tests can be incompatible based on resource allocation or chemistry. A processor may be used to gather the expected test panels for a period of time (e.g., an hour, a shift, or until an operator requests a change) and identify which tests within the panels may be incompatible. These tests can then be segregated between multiple analyzers to minimize incompatibilities. Reagents used by these tests can then be distributed manually or automatically to each analyzer to comply with the segregated allocation. Samples under test can then be serviced by the automation system and can be moved between appropriate analyzers to complete a test panel if the test panel requires tests that are on different analyzers.

As used herein, a test panel is a prescribed series of tests to be performed on a sample. Test panels can be unique to individual samples or may include a common combination of tests to be performed on multiple samples. Test panels may also include predetermined panels that can then be selected for a sample or group of samples. A test panel can include several routine tests that are performed on a plurality of samples, as well as specialized, less common tests that may be requested by laboratory to assist a doctor to diagnosis or assist a technician test for certain substances, such as for a drug test. A test panel can refer to all of the tests that will be performed by an analyzer or group of analyzers on a patient sample. Samples may undergo multiple types of test panels, such as hematological tests, chemical analysis tests, immunological tests, or the like. A sample undergoing chemistry analysis and immunological analysis can be said to have two test panels, including the chemistry test panel and the immunological test panel, or may be said to have a single test panel comprising chemical and immunological tests.

While embodiments are discussed herein with respect to dividing tests in a test panel across multiple analyzers, it should be understood that this division can include dividing tests amongst multiple standalone analyzers connected by an automation track or individual analyzer modules within a larger analyzer, where the modules may be connected via an automation track, which may or may not be built into the modules or added as a standalone automation system.

Each test of the test panel can utilize a plurality of instruments within an analyzer as well as one or more reagents. For example, a test may consist of aspiration of a portion of a patient sample, followed by aspiration of a first reagent to be mixed with the portion of the patient sample, followed by an incubation period to elicit a reaction, followed by a measurement of the reaction. Some tests may include multiple reagents that may be mixed with a portion of the patient sample. Each test can be calibrated on an analyzer using calibration samples. Tests that use the same methods as the calibration test can be used to provide accurate measurement of certain properties of patient samples. In order to comply with the calibration, the tests performed on a sample-under-test should comply with the procedures used in the calibration test. This can include utilizing substantially the same timing of steps during a calibration test and during a sample-under-test test.

The relative order and timing of all resources used by a given test can be referred to as a resource allocation table profile. A resource allocation test (RAT) profile allows a schedule of a test to be mapped to the various resources (e.g., pipette, incubator, etc.) within an analyzer in a given cycle to complete the test with prerequisite timing. In some embodiments, the requisite timing is used to guarantee that a given test falls within certain repeatability constraints so that each test complies with a calibration version of the test. In some embodiments, a test will not begin unless its entire RAT profile can be mapped to each resource in an analyzer, reserving that resource for the required future machine cycle. For example, where a test requires a second probe to be used on the next cycle after a first probe is used, the test will not begin using the first probe until the second probe can be reserved during the subsequent machine cycle. Two tests are said to have incompatible RAT profiles if they present a conflict that prevents the analyzer from launching a test every machine cycle. If an analyzer can launch a test every machine cycle, the analyzer can operate with optimal throughput.

FIG. 1 shows resource allocation schedules of two exemplary types of tests. Table 10 shows the resource allocation table for test A. The schedule for test A requires using a first probe P1, followed by a second probe P2 during the next machine cycle. Subsequently, test A requires use of an incubator for an additional machine cycle (or machine cycles), followed by a reading of results using a luminescence detector at a predetermined later machine cycle. As can be seen in table 10, multiple instances of test A can begin one after another, beginning each machine cycle. Test A2 can begin one machine cycle after test A1; test A3 can begin one machine cycle after test A2.

Table 12 shows resource allocation table for test B. The schedule for test B requires using the second probe P2, followed by the first probe P1 during the next machine cycle. Subsequently test B requires use of the incubator for an additional machine cycle (or machine cycles), followed by a reading of results using a luminescence detector at a predetermined later machine cycle. Similarly to test A, multiple instances of test B can be repeated beginning each machine cycle. Test B2 can begin one machine cycle after test B1; test B3 can then begin one machine cycle after test B2.

Table 14, however, shows the loss of throughput efficiency that can be encountered when tests A and B are operated on the same instruments. While tests A1 and B1 utilize a compatible schedule of probes, both tests A1 and B1 require use of the incubator during a third machine cycle. Accordingly, there is a resource allocation incompatibility between tests A1 and B1. Test B1 cannot begin until two machine cycles after test A1 begins. Otherwise, test B1 would have to wait for test A1 to complete using the incubator. Accordingly, there are machine cycles where resources within an analyzer are sitting idle. For example, probe P1 sits idle for machine cycles 2 and 3, as shown by the black boxes. When table 14 is compared to tables 10 and 12, it can be seen that during six machine cycles only two tests can be completed due to a resource allocation table incompatibility, as compared to the three tests that can be completed in six machine cycles where there is no resource allocation table incompatibility.

In other words, analyzers launching tests with the RAT profile of test A can launch a test every cycle. The total turnaround time of 300 tests, for instance, would be 303 machine cycles. Similarly, an analyzer launching only tests of the RAT profile of tests B could launch a test every cycle for a total turnaround time of 303 machine cycles for 300 tests. However, an analyzer performing 150 instances of test A and 150 instances of test B cannot launch a test every cycle due to the RAT-profile incompatibility of tests A and B. In a worst-case scenario, alternating tests A and B would result in a schedule of tests that produces a luminescence result every other machine cycle. The 300 total tests scheduled may take roughly twice as long (e.g., 605 cycles) as a group of tests that does not present a RAT-profile incompatibility. Accordingly, it is desirable to avoid scheduling tests A and B on the same analyzer during successive machine cycles.

As a practical matter, the reduced throughput due to incompatibilities can be mitigated by interleaving tests from multiple test panels, allowing tests to be grouped in time with other tests that do not present incompatibility. However, it is generally not practical to interleave the tests of more than a handful of samples. For example, five samples with a test panel consisting of test A and test B can be handled on a single analyzer, performing five instances of test A followed by five instances of test B.

Another type of incompatibility is a chemistry incompatibility between two tests. During a standard workflow, a reagent aspirating probe will aspirate different reagents each successive machine cycle. To prevent contamination, the aspirating step used by the reagent probe typically includes a brief wash cycle whereby water is sprayed on the probe tip and/or water is repeatedly aspirated and dispensed from the probe tip to rinse away any chemical residue left by the last reagent. For most reagents, a brief wash cycle is sufficient. However, certain combinations of reagents are more sensitive to cross contamination. Some reagents may react, such as acids and bases, and in some cases this reaction can be quite severe, possibly contaminating the second reagent container, causing an entire reagent pack to be ruined. Incompatible reagents are often characterized as a first aggressor reagent and a second victim reagent. A first reagent may be an aggressor reagent only for a handful of other victim reagents, rather than being a general aggressor. Similarly, a second reagent may be a victim reagent only for handful of other aggressor reagents. Therefore, an aggressor reagent may only create an incompatibility with other tests where the next test utilizes a corresponding victim reagent. Typically, two reagents can be an aggressor/victim combination, and the determination of which is the aggressor and victim depends only on which reagent is aspirated first (the aggressor) and second (the victim). Where successive tests include an aggressor reagent and a victim reagent, residue from the aggressor reagent left on a probe tip should be carefully washed away.

A typical solution to these incompatible reagents is to spend additional time washing the reagent probe after an aggressor reagent is dispensed and before a victim reagent is aspirated. This can take an additional machine cycle and therefore result in a process inefficiency, because the reagent probe is not available to participate in a test during that additional wash cycle. This is undesirable, and can be addressed in some embodiments.

FIG. 2 shows two exemplary test panels that include three tests each that are incompatible with other tests in the test panel due to RAT-profile incompatibility or chemical incompatibility. Exemplary test panel 1 includes three tests: test A (TA), test B (TB), and test C (TC). As shown in table 16, tests A and B are resource allocation table incompatible, like tests A and B in FIG. 1. Test C and test A are chemically incompatible because they use reacting reagents. Exemplary test panel 2 includes three additional tests: test D (TD); test E (TE); and test F (TF). As shown in table 18, tests F and D are RAT-profile incompatible, creating allocation conflicts when starting in succession. Tests E and F are chemically incompatible, using reactive reagents. If panel 1 is run on a single analyzer, the incompatibilities will prevent the analyzer from running all the tests in the panel in succession. Unless other samples have tests that are compatible without creating additional incompatibilities, the analyzer will be unable to begin a test each cycle, reducing the throughput of the analyzer as various instruments within the analyzer will be idle for multiple cycles. Similarly, running panel 2 on a second analyzer will create similar scheduling inefficiencies on the second analyzer.

FIG. 3 shows exemplary ways to allocate tests from panel 1 and panel 2 amongst two analyzers. A first allocation, shown in table 20 uses a traditional approach whereby all tests from a given test panel are run on the same analyzer. Where an automation system between analyzers is slow or unreliable, this method may be the only practical method of allocating tests. However, because of incompatibilities between tests A, B, and C, analyzer 1 may not be able to operate with optimal efficiency when executing panel 1. Similarly, analyzer 2 may not be able to operate with optimal efficiency due to incompatibilities between tests D, E, and F.

Table 22 shows a more optimal allocation of tests between analyzer 1 and 2 in accordance with some embodiments. By looking at table 16, it can be seen that test A should not be allocated to the same analyzer as tests B and C. However, tests B and C are both RAT-profile compatible and chemically compatible. Accordingly, tests B and C can be allocated to the same analyzer. Accordingly, samples-under-test using panel P1 can be handled by analyzer 1 and 2, rather than by a single analyzer. Because both analyzer 1 and 2 can be operating with optimal efficiency, the throughput may be increased, thereby reducing the overall time for which a sample-under-test must spend at each analyzer when samples arrive in a batch. This time savings may be sufficient to overcome the amount of time needed to traverse between analyzers 1 and 2 using the automation system.

Test panel P2 can be divided between analyzer one and analyzer two, as well. As can be seen in table 18, test F is incompatible with tests D and E, while tests D and E are both RAT-profile compatible and chemically compatible. Accordingly, test F can be allocated to analyzer 1, while tests D and E can be allocated to analyzer 2. In the allocation shown in table 22, samples within a batch that undergo test panel P1 or P2 will be handled by both analyzer 1 and analyzer 2. While each sample will be handled by two analyzers and will traverse the automation system between the analyzers, time savings can be accomplished because the throughput of each analyzer can be increased by eliminating or reducing incompatibilities between successive tests performed by each analyzer. For a sufficiently fast automation system and a sufficiently large batch of samples, the turnaround time of a batch of samples can be reduced using the distribution of tests shown in table 22.

In the prior art, conflicts such as the conflict between tests A and B (FIG. 1) could result in up to a 20% loss of throughput efficiency in a single analyzer setup. The typical prior art approach to allocating tests in multiple analyzer setups, even where an automation system is used between analyzers, has been to have all tests for a given sample performed by the same analyzer. A typical prior art automation system includes a friction belt-based automation system that moves samples between points. These friction track systems typically require hard singulation between samples, including hard stops. To avoid jarring samples and carriers, such as pucks, that hold samples while traversing the friction track, the friction belt typically moves at a velocity that is relatively slow compared to the cycle time of instruments in an analyzer. Furthermore, queues build up during operation at each singulation point, such that the travel time between two points depends largely on the number of samples that are traversing the friction track at any given point. This typically prevents guaranteed time of arrival when traversing the friction track. Accordingly, dividing test panels between multiple analyzers could prevent calculation of a guaranteed time of completion for a given sample once the first test has commenced.

However, as faster, more predictable automation systems become available for use in moving samples between analyzers or analyzer modules, the penalties of traversing an automation system during a test panel can be mitigated or removed. For example, automation systems that use fast, semi-autonomous carriers or those that use independently driven and/or independently routed carriers can be used to provide fast, reliable transit between analyzers or analyzer modules without requiring hard singulation stops and long queues that create latency when traversing an automation system. Similarly, in some embodiments, large groups of samples can be scheduled to move independently between analyzers or analyzer modules with reliability. Examples of automation systems that may be suitable for use with some embodiments to provide reliable and/or low latency between analyzers or analyzer modules can be found in PCT/US13/64630 and PCT/US13/24331, which have been incorporated herein by reference in their entirety. By utilizing a more reliable and faster automation system, it may be possible to reduce the travel time between two analyzers or analyzer stations, such that the additional time (e.g., latency) experienced by a sample as it traverses between analyzers is mitigated and overcome by the increase in throughput available due to minimizing lost cycles due to incompatibilities between subsequent tests.

FIG. 4 shows a comparison between two approaches to allocating tests within two analyzers using an exemplary automation system. In this example, an analyzer is capable of performing at optimal efficiency at a rate of 300 tests per hour. An exemplary panel of tests includes conflicts that create a 10% decrease in performance of the analyzer when the conflicting tests are performed by the same analyzer. A travel delay between analyzers is assumed to be 60 seconds. As shown in table 24, the allocation models depicted in FIG. 3 result in two different sloped lines when plotting the number of samples in a batch versus the turnaround time for the batch (measured as the time until the final aspiration has been performed on the last sample). Line 26 reflects the allocation scheme in table 20, whereby each sample is processed only by one analyzer. The steeper slope of line 26 reflects that the average turnaround time for each sample is longer due to the inefficiency caused by conflicts. However, because each sample stays within a single analyzer, the samples do not incur a sixty second penalty by traversing the automation system between analyzers. Line 28 reflects the allocation scheme in table 22, whereby tests are allocated between two analyzers to minimize conflicts. Line 28 has a gentler slope, reflecting that the average throughput of each analyzer is increased due to lack of conflicts. However, because each sample must be handled by two analyzers, each sample incurs a sixty second penalty by traversing the automation system. It should be noted, that in this example where a batch is greater than 16 samples, the turnaround time for a batch is faster using the allocation method shown in table 22. Meanwhile, for batch sizes less than 16 samples, the total turnaround time for a batch is less when using the allocation of tests shown in table 20. Accordingly, for larger batches, splitting test panels across analyzers to avoid conflicts can reduce the turnaround time of the sample batch, even though each sample must spend an additional minute traversing between two analyzers. As automation systems improve and reduce the total travel time between analyzers, the penalty for traversing the automation system can be reduced and smaller sample batches can benefit from the allocation of tests shown in table 22.

Figure 5:
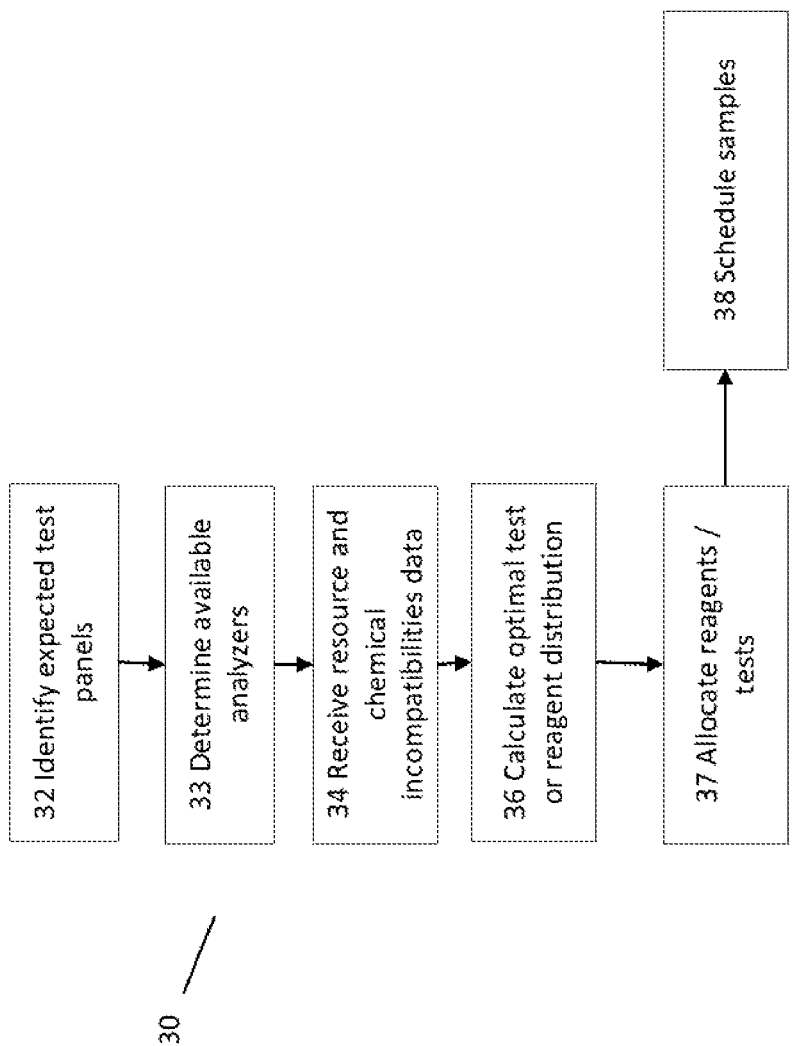
FIG. 5 is a flowchart depicting an exemplary method for allocating tests and/or reagents amongst a plurality of analyzers that may be used with some embodiments.

FIG. 5 depicts a method 30 for distributing and allocating tests across different analyzers in an optimal fashion. At step 32, one or more processors gather information about tests to be performed by a plurality of analyzers or analyzer modules. This allows the processor to identify a plurality of expected tests to be performed by a plurality of analyzer modules. This step can include receiving a list of scheduled tests for the plurality of samples from a laboratory information system, such as a manifest of test panels for a batch of samples. This may also include an expected list of test panels that may be generated in any suitable fashion, such as by experience, or by configuration. For example, the processor can identify a plurality of expected tests by analyzing statistics from past tests to determine an approximation of the likelihood of expected tests to be used by upcoming sample batches. For example, analyzers in a drug testing laboratory may routinely see test panels that test for certain sets of narcotics. When the analyzers are installed, an identification of the expected tests that will be performed by analyzers in the laboratory may be determined by configuration in a prepackaged software or set manually. In some embodiments, this step can include receiving, by the processor, input from an operator using a computerized interface. Similarly, a predetermined list of expected test panels may be configured at the factory when an analyzer is manufactured and may be updated via remote software updates or by user configuration. In some embodiments, an operator may load a batch file or manually select the tests to be run within a batch or a shift. In some embodiments, the processor may gather the information about the expected tests to be performed by communicating with a laboratory information system (LIS) that includes all of the tests to be performed for a plurality of patient samples. Accordingly, the expected tests to be performed may be a list of the actual tests to be performed. In some embodiments, this information can be obtained automatically through software interfaces that read manifests or LIS files, or by communicating with an LIS server. In some embodiments, this information can be predetermined or configured for a long period of time (such as the lifetime of the analyzers or until a system is reconfigured). In some embodiments, this information may be selected or input by an operator at the beginning of a shift or a batch or for any reasonable period during which samples are expected to undergo a set of predetermined test panels.

At step 33, one or more processors determine information about capabilities of available analyzers and/or modules within an analyzer that may be suitable for performing various tests in the test panels determined at step 32. In some embodiments, this step can include asking an operator to identify the make, model, and/or configuration of analyzers or analyzer modules that can be used to perform tests in the laboratory. This information can be input one time, such as at configuration of the analyzer system or maybe input along with test panel information in step 32, such as at the beginning of the batch or the beginning of a shift. This information can also be gathered from a configuration file or batch file that is predetermined prior to the arrival of a batch of samples. In some embodiments, this step can include receiving a list of the plurality of analyzer modules and capability information sufficient to determine which analyzer modules are capable of performing each of the plurality of expected tests from an LIS. This can be accomplished by querying a server that is part of an LIS environment via a network. When analyzers are installed and operational, these analyzers may be in communication with the LIS system via a network, allowing the LIS software to have a real-time understanding of the status and capabilities of analyzers in a laboratory.

In some embodiments, an automation system that couples a plurality of analyzers can provide this information about the capabilities of the analyzers serviced by the automation system to the LIS software or directly to the processors that allocate tests to analyzers. Using this information, processors performing method 30 can utilize real-time status information to determine how to properly allocate tests for a plurality of samples. In some embodiments, step 33 can include receiving, from a processor associated with at least a subset of the plurality of analyzers, capability information sufficient to determine whether that analyzer module is capable of performing each of the plurality of expected tests. In some embodiments, information about the makeup and capabilities of analyzers that can be used for the tests can be input manually by an operator via a user interface (e.g., a GUI or web interface) or by selection of a configuration file.

At step 34, one or more processors receive information about incompatibilities for various tests. This information can be in the form of resource allocation tables that may be suitable for identifying incompatibilities between various tests in the expected test panels determined at step 32. Chemical incompatibilities may be identified via a database that includes identification of which tests are incompatible with each other test. In some embodiments, a database is made available to the processor that includes one or more records for each possible test. Within each record in the database, a resource allocation table for the test can be provided, as well as an identification of which other tests are chemically incompatible. In some embodiments, the records include an identification of which other tests are resource allocation table incompatible, rather than, or in addition to, providing the resource allocation table for each test. RAT incompatibility information can be used to identify which tests are incompatible because they require allocation of resources in a conflicting manner. By providing identification of which tests are resource allocation table incompatible with the test in each record, an identification of incompatible tests can be done in a more computationally efficient manner. The incompatibility data may be presented via a local or remote database that may be part of an LIS system or may be part of a configuration file that is created or loaded manually.

At step 36, one or more processors calculate a substantially optimal distribution of tests or reagents amongst the available analyzers determined in step 33. The processor can identify an optimal distribution using any conventional search algorithm, such as a beam search, to identify a distribution of tests amongst the analyzers that minimizes conflicts. In some environments, local search algorithms or tree search algorithms may be used to identify local or global maximum solutions to optimize test efficiency by minimizing incompatibilities between tests. In some embodiments, the search algorithm can utilize a weighted heuristic that accounts for the number or frequency of the expected tests in evaluating the potential number of incompatibilities. In some embodiments, a threshold for a maximum number of incompatibilities on each analyzer can be used to quickly settle on a solution that provides a suitable distribution of tests. By choosing a suitable threshold, a substantially optimal distribution of tests may be discovered, without creating a computationally intensive search for an optimal distribution of tests to minimize incompatibilities. It should be appreciated that in some embodiments, it is desirable to determine a globally optimal solution that minimizes the number of incompatibilities, while in some embodiments a substantially optimal solution, such as one of several locally optimal or near optimal solutions may be suitable. For example, in some embodiments, a substantially optimal solution may be a distribution of tests that reduces the number of incompatibilities (in comparison to a distribution where all tests are performed by a single analyzer) by 50% or more. In some embodiments, the heuristics or thresholds used by the searching algorithm can be manually selected or configured via files loaded at runtime or during the setup of an analyzer system. In some embodiments, there may be a plurality of solutions of distributions of tests amongst analyzers that minimize incompatibilities. In some embodiments, solutions can be found that eliminate incompatibilities.

In some embodiments, the determination of which analyzer should receive reagents will drive which tests are available at each analyzer or analyzer module. Accordingly, in some embodiments, processors determining the allocation of tests amongst a plurality of analyzers can determine the allocation of reagents independently of allocating tests. In some embodiments, chemical incompatibilities amongst reagents can be used as the primary basis for determining where to locate reagents within a plurality of analyzers. In these embodiments, the algorithm for determining the optimal distribution of reagents may or may not consider resource allocation tables for tests. In some embodiments, the determination made by the algorithm may determine the distribution of reagents rather than tests. Later, another processor or algorithm determining the schedule of tests amongst a batch of samples may consider the distribution of reagents in determining on which analyzers to schedule each test in a panel of tests. This may allow the distribution of reagents to influence distribution of tests at a later time, without explicitly determining the distribution of tests during step 36.

At step 37, one or more processors allocate the tests or reagents to the plurality of analyzers or modules within an analyzer. In some embodiments, this can include instructing an operator to manually load reagent packs to each analyzer or analyzer module. This instruction can be displayed on a graphical user interface or may be available to an operator via a web interface, by illuminating panels on one or more analyzers, or by using any other suitable conventional interface. The display can request that an operator manually load reagents into each appropriate analyzer module.

In some embodiments, an automation system can be provided that may allow the processor to automatically direct reagents to be placed within each analyzer or analyzer module. In some embodiments, step 37 can include communicating with a robotic device to automatically load reagents into each of the plurality of analyzer modules. For example, a robot arm, such as a pick-and-place device, may be used to place reagent packs onto an automation track at the direction of the processor to automatically install the reagent pack in an appropriate analyzer or analyzer module. This automation system may be provided as part of the automation system that is used for shuttling samples between analyzers or may be a separate automation system that includes one or more centralized reagent stores.

In most laboratory environments, analyzers include many systems that make the machines relatively large. Laboratories typically cannot easily add space to the room that houses analyzers. Accordingly, it may be desirable to limit the amount of space used to store reagents within an analyzer or analyzer modules. Accordingly, it may be desirable to limit the number of reagents or reagent packs that are stored at any given time within an analyzer or analyzer module. In some embodiments, one or more centralized reagent repositories can be used that store reagents when not in use. This can be, for example, a refrigerated area that is accessible to an automation system or to an operator. At step 37, software can direct the placement of reagent packs from a storage area into each selected analyzer or analyzer module. Software operating on the processor can instruct an operator to facilitate the transfer of reagents from the storage area to an analyzer manually or may direct components of an automation system to move reagents from the storage area to each analyzer or analyzer module in an automated fashion.

At step 38, one or more processors schedule tests for individual samples within a batch of samples. This can be performed by a different processor or set of processors than the processor or set of processors used to perform steps 32 through 37. For example, an allocation processor, which operates as part of an operator's workstation, can be used to perform steps 32 through 37, while a scheduling processor that is part of an automation system can be used to perform step 38. In some embodiments, a common processor is used, where steps 32 through 38 are performed by, or at the direction of, the automation system. Samples may be scheduled in any suitable manner, including determining which tests should be performed for each sample based on a sample batch manifest received from an LIS system or from operator input. Once a manifest of tests is determined, a scheduling processor may determine which tests are available at each analyzer or analyzer module. This determination can be in response to the allocation of tests performed at step 37. In some embodiments, the scheduling processor can determine which analyzers to use for each test based on a list of available reagents where reagents have been allocated at step 37. Accordingly, at step 37, reagents or tests may be directly allocated, which may influence the scheduling of tests at step 38. In some embodiments, step 38 can include dispatching each of the plurality of samples in a sample batch to at least one analyzer module to have at least one test performed by the analyzer module.

Samples may be scheduled in a first-in first-out (FIFO) manner or based on a priority. In some embodiments, common reagents for common tests may be redundantly distributed to a plurality of analyzers. This may allow the processor at step 38 to schedule samples with STAT priority to be handled by a single analyzer in most situations. While operating a sample in a single analyzer may increase test incompatibilities with other samples, the turnaround time of a STAT sample may be improved in some situations, which may be desirable even where handling of the STAT sample reduces the overall efficiency of the analyzer system.

It should be appreciated that, in some embodiments, multiple redundant analyzers may be used, such that allocation of tests or scheduling of tests can minimize incompatibilities on a plurality of analyzers, while allowing a scheduling processor to choose between multiple analyzers that have the same available tests. This may allow additional throughput to be added to an analyzer system by adding additional analyzers or analyzer modules, without introducing incompatibilities, and while allowing load-balancing of analyzer modules.

It should also be appreciated that the steps in FIG. 5 can be performed using software executing on one or more processors. In some embodiments, method 30 may be implemented via a software package that is loaded onto an automation system for execution on a processor used by the automation system. In some embodiments, dedicated circuits can perform one or more steps in method 30. For example, dedicated ASICs or FPGAs may be utilized to perform processing steps directly in hardware rather than relying on software instructions operating on a processor. Furthermore, one or more steps in method 30 may be performed using a combination of a processor acting as a controller and one or more electronic circuits that act in response to the processor. For example, step 37 may include dedicated circuitry and electro-mechanical devices that can physically allocate reagents between analyzers in response to the instruction to allocate reagents received from the processor.

Figure 6:
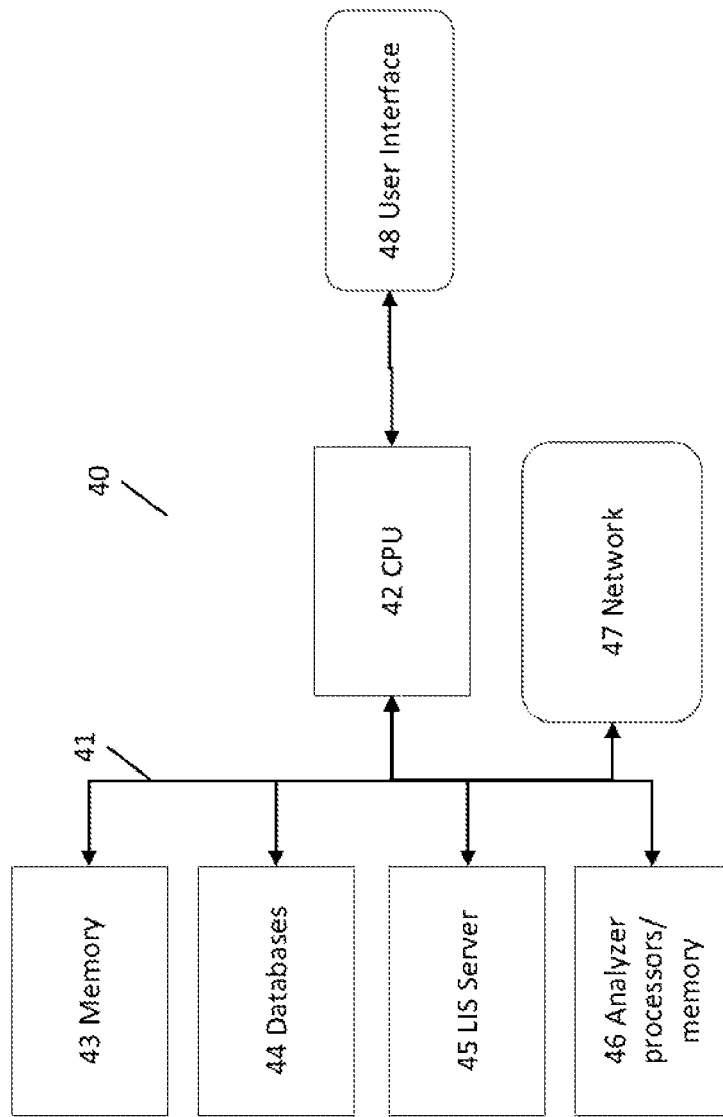
FIG. 6 is a system diagram depicting an exemplary system for allocating tests and/or reagents amongst a plurality of analyzers that may be used with some embodiments.

FIG. 6 shows an exemplary system 40 that may be suitable for use with certain embodiments, including that shown in FIG. 5. A processor 42 can perform each of the steps needed to allocate reagents to analyzers and schedule samples to be tested on each analyzer or analyzer module. Processor 42 may be any suitable type of processor, such as a RISC-based processor. Processor 42 may access resources via bus 41. Bus 41 may be an internal bus to a computer or may include a network and network adapter hardware that allows CPU 42 to communicate with resources on a network or local resources.

Memory 43 may include data and instruction memory that may be used by the processor. Data instruction may include other software routines beyond the methods discussed herein. Memory 43 may include instructions suitable for performing the steps in method 30. Databases 44 may provide information used by CPU 42 for performing steps in accordance with some embodiments. For example, databases 44 may include test manifests and incompatibility data about tests in test panels. In some embodiments, databases 44 may be accessed on a network and may be updated via an LIS system. LIS server 45 may be another computer or a software component, such as a server, that provides LIS functionality. This can allow CPU 42 to interact with information systems in the laboratory environment, allowing CPU 42 to access updated information about patient samples, procedures, tests, incompatibilities, etc. CPU 42 may also operate responsive to requests made by LIS server 45.

Block 46 can include the analyzer and automation system hardware and processors that CPU 42 may interact with. For example, CPU 42 may interact with analyzers and their processors to determine the capabilities of each analyzer, including the available reagents. Similarly, processor 42 may interact with a reagent store to determine the current inventory of reagents and use this information to allocate reagents to analyzers. Interaction with analyzers in block 46 may be through any suitable method including remote procedure calls, APIs, or network interfaces presented to processor 42.

Network 47 may be an internal network or an external network, such as the Internet, that provides a network interface for CPU 42 to receive updates, instructions from an operator or technician, or any other suitable communication that may be useful in performing steps of certain embodiments. User-interface 48 can provide a visual interface locally to an operator of an automation system or analyzer system. User-interface 48 may be used for any of the purposes disclosed herein. Network 47 may also be used to provide a web-based interface for accessing test menus via the Internet, allowing operators remotely or locally on the network to direct the operation of processor 42.

Figure 7:
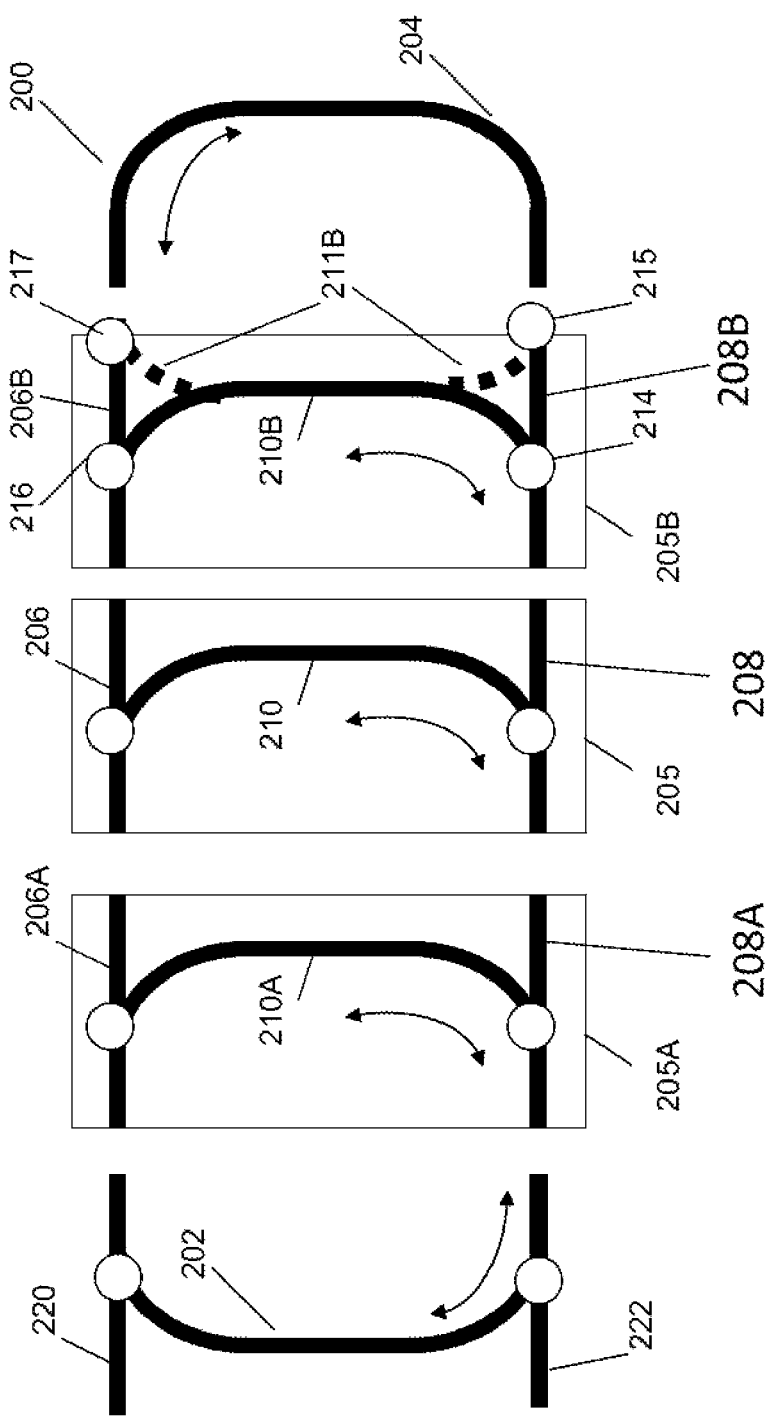
FIG. 7 is a diagrammatic view of an exemplary modular track configuration that can be used with the embodiments disclosed herein.

FIG. 7 shows a modular approach to an automation system track that can be used for certain embodiments of the present invention. In this example, the tracks may be integrated into individual analyzer stations/modules, such that the track can be used as part of the internal motion or sample handling system of individual lab stations. It should be appreciated that the allocation techniques described herein can allow allocation of samples to different analyzers within a larger system, such as a work-cell, or to different analyzer modules within a modular analyzer. When referring to allocating sample tests or reagents to analyzers, the term should be considered inclusive of allocating sample tests or reagents to modules within an analyzer where multiple modules are otherwise capable of performing the test being allocated.

In some embodiments, multiple different types of motion systems may be used within different analyzer/testing stations. For example, some stations can include friction tracks for shuttling pucks or trays of sample tubes, and may include carousels containing smaller vessels, such as cuvettes and reaction vessels, into which portions of the sample can be aspirated and dispensed. In some embodiments, by integrating portions of the track system into the analyzer stations themselves, each station can include its own queuing logic and may be simplified to eliminate unnecessary internal motion systems.

In some embodiments, track 200 can be broken into modular components that are integrated into analyzer modules. In this exemplary track, modules 205, 205A, and 205B can be combined with one another and optionally other modular track components 202 and 204 to form a single track. For instance, 205A can be a module that performs immunoassay, clinical chemistry, ISE electrolyte testing, or the like. In some embodiments, all or a subset of these modules can have redundant capabilities when equipped with suitable reagents. In this example, the main outer track can be formed by track segments 202, 204, 206, 206A, 206B, 208, 208A, and 208B. Within the analyzer modules 205, 205A, and 205B, internal paths 210, 210A, and 210B form pullouts from the main track. The internal paths can be used for internal queuing and can be managed independently within each analyzer module to allow each module to have greater control over samples to be processed.

One advantage of integrating track 200 and sub-paths 210, 210A, and 210B into the analyzer modules 205, 205A, and 205B, respectively, may be that the internal handling mechanisms within each analyzer module can be specially adapted to better coordinate with the track sub-paths. In some embodiments, modules 205, 205A, and 205B can be adapted to process each sample within a period that is less than an operation cycle of the overall analyzer, leaving enough time for the sample to be routed along the track system to another module after processing, allowing the other module to immediately process the sample on the next operation cycle. As used herein, an operation cycle is a unit of time used by scheduling algorithms to allot processing time to modules for sample assays. These can be dynamic or fixed and can allow synchronous operation of the modules in the analyzer and provide a reliable timing model for scheduling samples amongst multiple modules in the analyzer. The operation cycle time can be chosen to be the time needed by any given module between when it starts processing a first sample, and when it is ready to process another sample under expected steady-state conditions. For example, if an analyzer can process one test every three seconds, and the expected average tests per sample is seven, the operation cycle time can be 21 seconds. It should be understood that individual modules can implement efficiency techniques, such as parallelism or processing multiple samples within a cycle, to maximize throughput, even when the number of tests-per-sample varies from an expected amount. Furthermore, it should be understood that in some embodiments, individual modules have different operation cycle times, and these modules can operate substantially asynchronously from one another. Virtual queues or buffers can be used to assist the management of sample scheduling where cycle times or demand vary between modules. In some embodiments, the cycle time for moving samples between modules is more than the cycle time used with a module to perform individual steps for a test. In some embodiments, the total transit time between analyzer modules is substantially less than a minute, allowing a single test panel to be completed using multiple analyzer modules, while allowing a reduction of the total turnaround for many expected sample-batch sizes.

Figure 8:
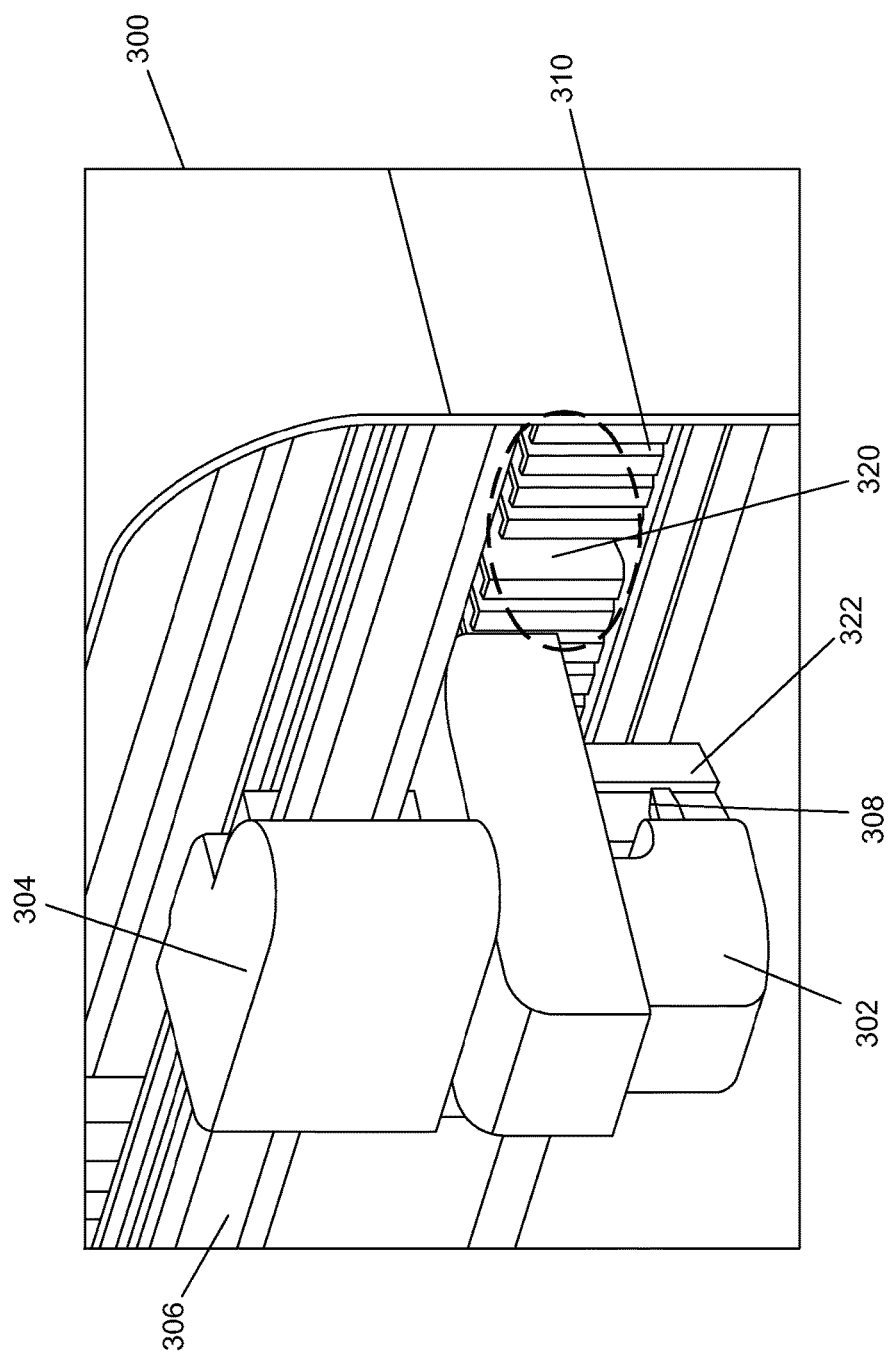
FIG. 8 is a perspective view of an exemplary loading device that may be used to stock analyzers with reagents responsive to the determined allocation of reagents or tests amongst a plurality of analyzers or modules in accordance with some embodiments disclosed herein.

FIG. 8 shows an exemplary embodiment of a pick-and-place robot for extracting reagent packs from storage to be delivered to an appropriate analyzer or analyzer module as determined by a processor. By utilizing a pick-and-place robot that may be controlled by processor, reagents may be delivered automatically to analyzers or modules responsive to a desired allocation of reagents. Reagent storage area 300 can include a robot arm 302 and a reagent storage drawer 310. Robot arm 302 travels along the track 306 using carriage 304. This can allow the robot effectors 308 to be positioned at an appropriate reagent sample pack within drawer 310. Robot arm 304 may then use the effectors to select and grab an appropriate reagent pack. Robot arm 304 may then travel along track 306 to an analyzer to place the reagent pack within the analyzer or it may place the reagent pack onto a carrier on an automation system, such as the same automation system used to transport samples, to allow delivery via an automation system to a station within a targeted analyzer module. Once the reagent pack arrives at the module, another pick-and-place device may remove the reagent pack from an automation track and place it in an appropriate part of the targeted module, to allow the reagent pack to be used for testing. Drawer 310 can include a plurality of cartridges 320. A selected cartridge 322 may be removed via robot arm 302 for delivery to an appropriate analyzer.

Other suitable robots may be used for automatically deploying reagents, including robot arms having articulated joints, plunger devices, actuators that dispense reagent cartridges from storage to a carrier or track, or the like.

While some embodiments make use of allocation schemes to improve the throughput of tests on samples when using automation systems, it should be appreciated that some embodiments can utilize the allocation schemes described herein to optimize throughput on systems that do not use an automation system. On systems that utilize a manual allocation of reagents and manually load samples onto different instruments, the selection of which reagents to load and which samples to assign to each instrument may be in accordance with the allocation schemes described throughout. In some embodiments, a computer program operating on a processor in the laboratory can receive test panels from an LIS server periodically, such as at the beginning of a shift. The program can analyze the tests requested in those panels and allocate tests (and thereby the reagents) to different instruments, as described throughout. An operator can be automatically given a manifest of which reagents to load into each analyzer and subsequently which samples to place in which analyzer. In some embodiments, an operator can see an update on a display that reflects the allocation of test panels and reagents amongst analyzers, automatically once a processor receives the test panels for a batch of incoming samples (e.g., at the beginning of a shift). In some embodiments, analyzers can determine an inventory of reagents, and request additional reagents or display a warning to an operator if the inventory of reagents is insufficient to comply with the optimized allocation of reagents based on the test panels. This can result in an optimized throughput of the analyzers in the lab, even where there is no automation system used.

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

What is claimed is:

1. A method for distributing sample tests in an IVD environment comprising:
   identifying a plurality of expected tests to be performed by a plurality of analyzer modules on a plurality of patient fluid samples stored in sample vessels;
   determining information about the capabilities of the plurality of analyzer modules;
   receiving, at a processor, incompatibility data identifying which of the plurality of expected tests are incompatible, where two tests within the plurality of expected tests are identified as incompatible when a pipette that interacts with the plurality of patient fluid samples would need to spend at least one cycle doing one of sitting idle due to a resource allocation conflict between the two tests and performing a washing operation due to a chemistry conflict between the two tests;
   calculating, by the processor, using the incompatibility data, a distribution of the plurality of expected tests amongst the plurality of analyzer modules that minimizes both resource allocation conflicts and chemistry conflicts;
   allocating reagents to each of the plurality of analyzer modules by selectively distributing a plurality of reagents to each of the plurality of analyzer modules in accordance with the calculated distribution of expected tests;
   scheduling the plurality of patient fluid samples to undergo tests at the plurality of analyzer modules in accordance with the calculated distribution of expected tests; and
   moving the sample vessels via an automation system such that at least a subset of the plurality of patient fluid samples each undergo tests by at least two of the plurality of analyzer modules to complete a plurality of test panels in accordance with the scheduling step,
   wherein the step of calculating a distribution of the plurality of expected tests comprises using a search algorithm to identify at least one solution that exceeds a compatibility threshold.

2. The method of claim 1, wherein the step of identifying a plurality of expected tests comprises receiving a list of scheduled tests for the plurality of patient fluid samples from a laboratory information system.

3. The method of claim 1, wherein the step of identifying a plurality of expected tests comprises analyzing statistics from past tests to determine an approximation of the likelihood of expected tests to be used by upcoming patient fluid sample batches.

4. The method of claim 1, wherein the step of identifying a plurality of expected tests comprises receiving, by the processor, input from an operator using a computerized interface.

5. The method of claim 1, wherein the step of determining information about the capabilities of the plurality of analyzer modules comprises receiving, from a laboratory information system, a list of the plurality of analyzer modules and capability information sufficient to determine which analyzer modules are capable of performing each of the plurality of expected tests.

6. The method of claim 1, wherein the step of determining information about the capabilities of the plurality of analyzer modules comprises receiving, from a processor associated with at least a subset of the plurality of analyzers, capability information sufficient to determine whether each analyzer module is capable of performing each of the plurality of expected tests.

7. The method of claim 1, wherein the step of allocating reagents comprises displaying a request to an operator to manually load reagents into each of the plurality of analyzer modules.

8. The method of claim 1, wherein the step of allocating reagents comprises communicating with a robotic device to automatically load reagents into each of the plurality of analyzer modules.

9. The method of claim 1, wherein the step of scheduling the plurality of patient fluid samples to undergo tests comprises scheduling higher priority patient fluid samples within the plurality of patient fluid samples to have all tests in a test panel performed by a single analyzer module.

10. A system for performing tests in an IVD environment, comprising:
    a plurality of analyzer modules, each configurable to perform a respective plurality of tests, wherein at least a subset of the analyzer modules are configurable to perform the same tests;
    an automation system configured to transport patient fluid samples between the plurality of analyzer modules; and
    at least one processor configured to perform steps of:
       identifying a plurality of expected tests to be performed by the plurality of analyzer modules on a plurality of patient fluid samples stored in sample vessels;
       determining information about the capabilities of the plurality of analyzer modules;
       receiving incompatibility data reflecting which of the plurality of tests are incompatible, where two tests within the plurality of expected tests are identified as incompatible when a pipette that interacts with the plurality of patient fluid samples would need to spend at least one cycle doing one of sitting idle due to a resource allocation conflict between the two tests and performing a washing operation due to a chemistry conflict between the two tests;
       calculating, using the incompatibility data, a distribution of the plurality of expected tests amongst the plurality of analyzer modules that minimizes both resource allocation conflicts and chemistry conflicts;
       allocating reagents to each of the plurality of analyzer modules by facilitating distribution of a plurality of reagents to selected analyzer modules in accordance with the calculated distribution of expected tests;
       scheduling a plurality of patient fluid samples to undergo tests at the plurality of analyzer modules in accordance with the calculated distribution of expected tests; and facilitating movement of sample vessels via the automation system such that at least a portion of the patient fluid samples undergo tests at more than one of the plurality of analyzer modules to complete a plurality of test panels in accordance with the scheduling step, wherein the step of calculating a distribution of the plurality of expected tests comprises using a search algorithm to identify at least one solution that exceeds a compatibility threshold.

11. The system of claim 10, wherein the step of identifying a plurality of expected tests comprises receiving a list of scheduled tests for the plurality of patient fluid samples from a laboratory information system.

12. The system of claim 10, wherein the step of identifying a plurality of expected tests comprises analyzing statistics from past tests to determine an approximation of the likelihood of expected tests to be used by upcoming patient fluid sample batches.

13. The system of claim 10, wherein the step of identifying a plurality of expected tests comprises receiving, by the processor, input from an operator using a computerized interface.

14. The system of claim 10, wherein the step of determining information about the capabilities of the plurality of analyzer modules comprises receiving, from a laboratory information system, a list of the plurality of analyzer modules and capability information sufficient to determine which analyzer modules are capable of performing each of the plurality of expected tests.

15. The system of claim 10, wherein the step of determining information about the capabilities of the plurality of analyzer modules comprises receiving, from a processor associated with at least a subset of the plurality of analyzers, capability information sufficient to determine whether each analyzer module is capable of performing each of the plurality of expected tests.

16. The system of claim 10, wherein the step of allocating reagents comprises displaying a request to an operator to manually load reagents into each of the plurality of analyzer modules.

17. The system of claim 10, wherein the step of allocating reagents comprises communicating with a robotic device to automatically load reagents into each of the plurality of analyzer modules.

18. The system of claim 10, wherein the step of scheduling the plurality of patient fluid samples to undergo tests comprises scheduling higher priority patient fluid samples within the plurality of patient fluid samples to have all tests in a test panel performed by a single analyzer module.

19. A non-transient machine-readable media containing instructions that configure a processor in an IVD environment to perform steps of:

identifying a plurality of expected tests to be performed by a plurality of analyzer modules on a plurality of patient fluid samples stored in sample vessels;

determining information about the capabilities of the plurality of analyzer modules;

receiving, at the processor, incompatibility data reflecting which of the plurality of tests are incompatible, where two tests within the plurality of expected tests are identified as incompatible when a pipette that interacts with the plurality of patient fluid samples would need to spend at least one cycle doing one of sitting idle due to a resource allocation conflict between the two tests and performing a washing operation due to a chemistry conflict between the two tests;

calculating, by the processor using the incompatibility data, a distribution of the plurality of expected tests amongst the plurality of analyzer modules that minimizes both resource allocation conflicts and chemistry conflicts;

allocating reagents to each of the plurality of analyzer modules by selectively distributing a plurality of reagents to each of the plurality of analyzer modules in accordance with the calculated distribution of expected tests;

scheduling a plurality of patient fluid samples to undergo tests at the plurality of analyzer modules in accordance with the calculated distribution of expected tests; and facilitating movement of sample vessels via the automation system such that at least a portion of the patient fluid samples undergo tests at more than one of the plurality of analyzer modules to complete a plurality of test panels in accordance with the scheduling step, wherein the step of calculating a distribution of the plurality of expected tests comprises using a search algorithm to identify at least one solution that exceeds a compatibility threshold.

* * * * *